US012733832B2

(12) United States Patent
Ng

(10) Patent No.: US 12,733,832 B2
(45) Date of Patent: Sep. 15, 2026

(54) BIO-IMPEDANCE MEASUREMENT DEVICE AND BIO-IMPEDANCE MEASUREMENT METHOD

(71) Applicant: Serial microelectronics information limited, Taipei City (TW)

(72) Inventor: Si Herng Ng, Hsinchu County (TW)

(73) Assignee: Serial microelectronics information limited, Taipei City (TW)

( * ) Notice: Subject to any disclaimer, the term of this patent is extended or adjusted under 35 U.S.C. 154(b) by 283 days.

(21) Appl. No.: 18/582,679

(22) Filed: Feb. 21, 2024

(65) Prior Publication Data

US 2025/0261872 A1 Aug. 21, 2025

(51) Int. Cl.
*A61B 5/053* (2021.01)
*A61B 5/00* (2006.01)
*A61B 5/0537* (2021.01)

(52) U.S. Cl.
CPC .......... *A61B 5/0537* (2013.01); *A61B 5/7225* (2013.01)

(58) Field of Classification Search
CPC ..... A61B 5/053; A61B 5/0531; A61B 5/0537; A61B 5/7225; A61B 5/7228
USPC .......................................................... 600/547
See application file for complete search history.

(56) References Cited

U.S. PATENT DOCUMENTS

| | | | | |
|---|---|---|---|---|
| 11,729,880 B1 * | 8/2023 | Thompson | H05B 47/10 315/302 |
| 12,635,896 B2 * | 5/2026 | Ng | A61B 5/053 |
| 2004/0158167 A1 * | 8/2004 | Smith | A61B 10/0041 600/547 |
| 2005/0151545 A1 * | 7/2005 | Park | G01R 27/02 324/679 |
| 2014/0128765 A1 * | 5/2014 | Chetelat | A61B 5/7207 600/547 |
| 2018/0067063 A1 * | 3/2018 | Cherkassky | G01R 19/0038 |
| 2018/0067154 A1 * | 3/2018 | Cherkassky | A61B 5/7235 |
| 2018/0284170 A1 * | 10/2018 | Barrettino | G01R 27/26 |
| 2020/0253500 A1 * | 8/2020 | Ha | A61B 5/0535 |
| 2021/0389354 A1 * | 12/2021 | Huynh | G01R 27/02 |

FOREIGN PATENT DOCUMENTS

| | | | |
|---|---|---|---|
| CN | 110974182 A * | 4/2020 | A61B 5/224 |
| EP | 4074370 A1 * | 10/2022 | H02M 7/53871 |

* cited by examiner

*Primary Examiner* — Adam J Eiseman
(74) *Attorney, Agent, or Firm* — Winston Hsu

(57) ABSTRACT

A bio-impedance measurement device includes a signal generator, configured to input a probing signal having a first frequency and an over-sampling pattern into a bio-impedance; a receiver, configured to receive a first response signal related to the probing signal from the bio-impedance; a demodulation circuit, coupled to the receiver, configured to generate a first in-phase signal and a first quadrature-phase signal according to the first response signal; and a processor, coupled to the signal generator and the demodulation circuit, configured to analyze the probing signal, the first in-phase signal and the first quadrature-phase signal to determine a bio-impedance value of the bio-impedance.

10 Claims, 10 Drawing Sheets

BIO-IMPEDANCE MEASUREMENT DEVICE AND BIO-IMPEDANCE MEASUREMENT METHOD

BACKGROUND OF THE INVENTION

1. Field of the Invention

The present invention relates to a bio-impedance measurement device and a bio-impedance measurement method, and more particularly, to a bio-impedance measurement device and a bio-impedance measurement method that utilize a probing signal having an over-sampling pattern to measure a bio-impedance value.

2. Description of the Prior Art

A bio-impedance measurement device is used to gauge the impedance of a user's body at a specific frequency. The bio-impedance measurement device introduces a probing signal into the user's body, measures a response signal related to the probing signal, computes the impedance value based on the response signal, and analyzes the impedance value to determine body compositions such as body fat and muscle mass. However, the impedance value includes a resistive part, a capacitive part and an inductive part. A conventional bio-impedance measurement device exhibits good measurement accuracy for the resistive part of the impedance value, but has poor measurement accuracy for the capacitance part and the inductance part of the impedance value. Therefore, how to enhance the measurement accuracy of the impedance value has become one of the goals in the industry.

SUMMARY OF THE INVENTION

Therefore, the purpose of the present invention is to provide a bio-impedance measurement device and a bio-impedance measurement method to improve the drawback of the prior art.

The embodiment of the present invention discloses a bio-impedance measurement device, comprising a signal generator, configured to input a probing signal having a first frequency and an over-sampling pattern into a bio-impedance; a receiver, configured to receive a first response signal related to the probing signal from the bio-impedance; a demodulation circuit, coupled to the receiver, configured to generate a first in-phase signal and a first quadrature-phase signal according to the first response signal; and a processor, coupled to the signal generator and the demodulation circuit, configured to analyze the probing signal, the first in-phase signal and the first quadrature-phase signal to determine a bio-impedance value of the bio-impedance.

The embodiment of the present invention discloses a bio-impedance measurement method, comprising inputting a probing signal having a first frequency and an over-sampling pattern into a bio-impedance; receiving a first response signal related to the probing signal from the bio-impedance; generating a first in-phase signal and a first quadrature-phase signal according to the first response signal; and analyzing the probing signal, the first in-phase signal and the first quadrature-phase signal to determine a bio-impedance value of the bio-impedance.

These and other objectives of the present invention will no doubt become obvious to those of ordinary skill in the art after reading the following detailed description of the preferred embodiment that is illustrated in the various figures and drawings.

DETAILED DESCRIPTION

Certain terms are used throughout the description and following claims to refer to particular components. As one skilled in the art will appreciate, hardware manufacturers may refer to a component by different names. This document does not intend to distinguish between components that differ in name but not function. In the following description and in the claims, the terms "include" and "comprise" are utilized in an open-ended fashion, and thus should be interpreted to mean "include, but not limited to". Also, the term "couple" is intended to mean either an indirect or direct electrical connection. Accordingly, if one device is coupled to another device, that connection may be through a direct electrical connection, or through an indirect electrical connection via other devices and connections.

Figure 1:
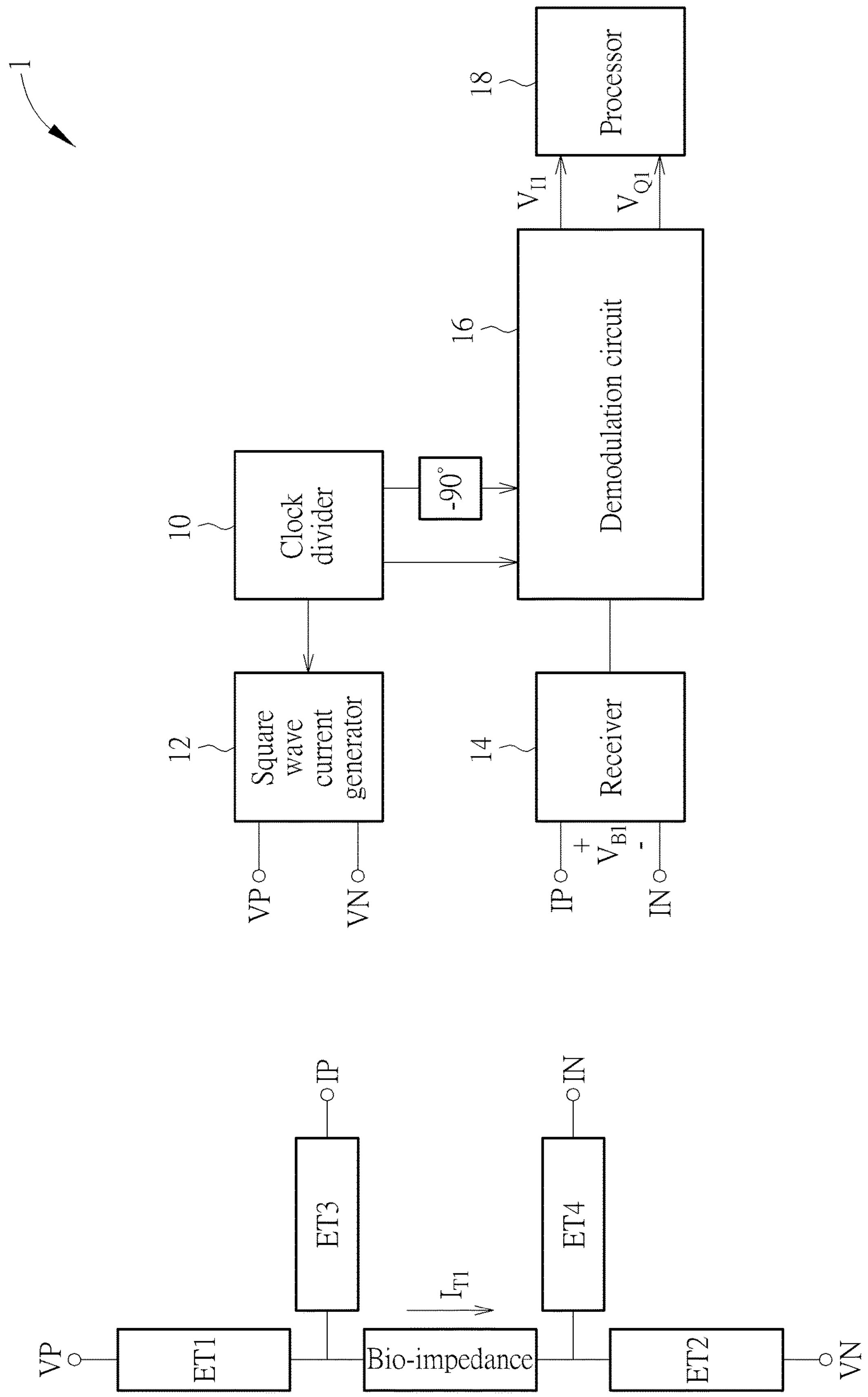
FIG. 1 is a schematic diagram illustrating a case tampering detection device with a conventional structure.

Please refer to FIG. 1. FIG. 1 is a schematic diagram of a conventional bio-impedance measurement device 1. The bio-impedance measurement device 1 may input a probing signal of a specific frequency into a bio-impedance, receive a response signal related to the probing signal from the bio-impedance, and analyze the response signal to determine a bio-impedance value of the bio-impedance. The bio-impedance measurement device 1 includes a clock divider 10, a square wave current generator 12, a receiver 14, a demodulation circuit 16 and a processor 18. The clock divider 10 is configured to provide clock signals of the specific frequency to the square wave current generator 12 and the demodulation circuit 16. The square wave current generator 12 is configured to generate the probing signal $I_{T1}$ according to the clock signals, and input the probing signal $I_{T1}$ of the specific frequency into the bio-impedance through electrodes ET1, ET2. The receiver 14 is configured to receive the response signal $V_{B1}$ related to the probing signal $I_{T1}$ from the bio-impedance through electrodes ET3, ET4. In an embodiment, the response signal $V_{B1}$ may be expressed as the equation (1):

$$V_{B1} = I_{T1} \times \frac{4}{\pi}\left[|Z(\omega)|\sin(\omega t + \theta_{\omega}) + \frac{1}{3}\left[|Z(3\omega)|\sin(3\omega t + \theta_{3\omega}) + \frac{1}{5}[|Z(5\omega)|\sin(5\omega t + \theta_{5\omega}) + \dots\right]\right] \quad (1)$$

where $V_{B1}$ represents the response signal, $I_{T1}$ represents the probing signal, ω represents the angular frequency of the specific frequency, Z(nω) represents the bio-impedance value when the angular frequency is nω, and $\theta_{n\omega}$ represents the phase of bio-impedance value when the angular frequency is nω.

The demodulation circuit 16 is coupled to the clock divider 10 and the receiver 14, and configured to generate an in-phase signal $V_{I1}$ and a quadrature-phase signal $V_{Q1}$ according to the clock signals and the response signal $V_{B1}$. The processor 18 is coupled to the demodulation circuit 16, and configured to analyze the probing signal $I_{T1}$, the in-phase signal $V_{I1}$ and the quadrature-phase signal $V_{Q1}$ to determine the bio-impedance value Z(nω). In an embodiment, the in-phase signal $V_I$n may be expressed as the equation (2):

$$V_{I1} = I_{T1}|Z(\omega)|\cos(\theta_{\omega}) \times \frac{8}{\pi^2}\left[1 + \frac{1}{9}\frac{|Z(3\omega)|}{|Z(\omega)|}\frac{\cos(\theta_{3\omega})}{\cos(\theta_{\omega})} + \frac{1}{25}\frac{|Z(5\omega)|}{|Z(\omega)|}\frac{\cos(\theta_{5\omega})}{\cos(\theta_{\omega})} + \dots\right] \quad (2)$$

where $V_{I1}$ represents the in-phase signal, $I_{T1}$ represents the probing signal, ω represents the angular frequency of the specific frequency, Z(nω) represents the bio-impedance value when the angular frequency is nω, and $\theta_{n\omega}$ represents the phase of bio-impedance value when the angular frequency is nω.

Figure 2:
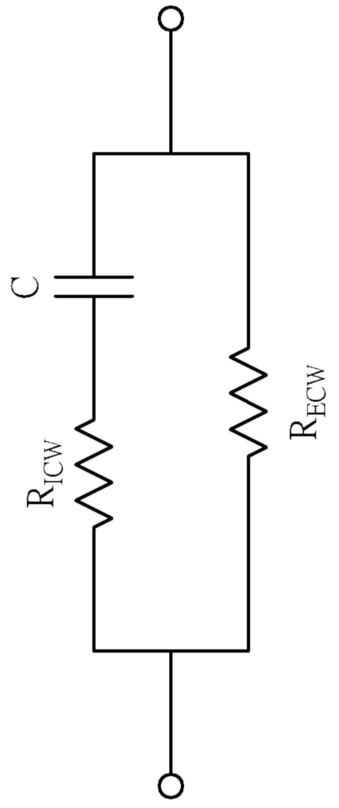
FIG. 2 is a schematic diagram illustrating a model of a bio-impedance.

It should be noted that the bio-impedance value Z(nω) may include a resistive part, a capacitive part and an inductive part. The high-order terms Z(3ω), Z(5ω), etc. of the bio-impedance value Z(nω) in the equation (2) show that the bio-impedance has the capacitive part and the inductive part. The high-frequency terms may cause an error of 1-5% in the bio-impedance value measured by the bio-impedance measurement device 1. For example, the bio-impedance is modeled as the resistance $R_{ICW}$, $R_{ECW}$ and the capacitance C as shown in FIG. 2. If $R_{ICW}$ and $R_{ECW}$ are equal to 800 ohm and the capacitance C is equal to 0.7 nF, the error in the bio-impedance value Z (nω) measured by the bio-impedance measurement device 1 is equal to 3.58%. In another example, if the bio-impedance is modeled as a pure resistance and has no capacitive part and inductive part, that is, $\theta_{n\omega}$=0 and $\cos(\theta_{nw})$=1, the equation (2) may be simplified to the equation (3)

$$V_{I1} = I_{T1} \times R \quad (3)$$

where $V_{I1}$ represents the in-phase signal, $I_{T1}$ represents the probing signal, and R represents the bio-impedance value.

Since the probing signal $I_{T1}$ is a known value, the bio-impedance value R may be calculated according to the measured in-phase signal $V_{I1}$ and the probing signal $I_{T1}$. It should be noted that the error in the bio-impedance value R measured by the bio-impedance measurement device 1 may less than 0.1%.

In short, the bio-impedance measurement device 1 has a larger error in measuring the bio-impedance including the resistive part, the capacitive part and the inductive part.

Figure 3:
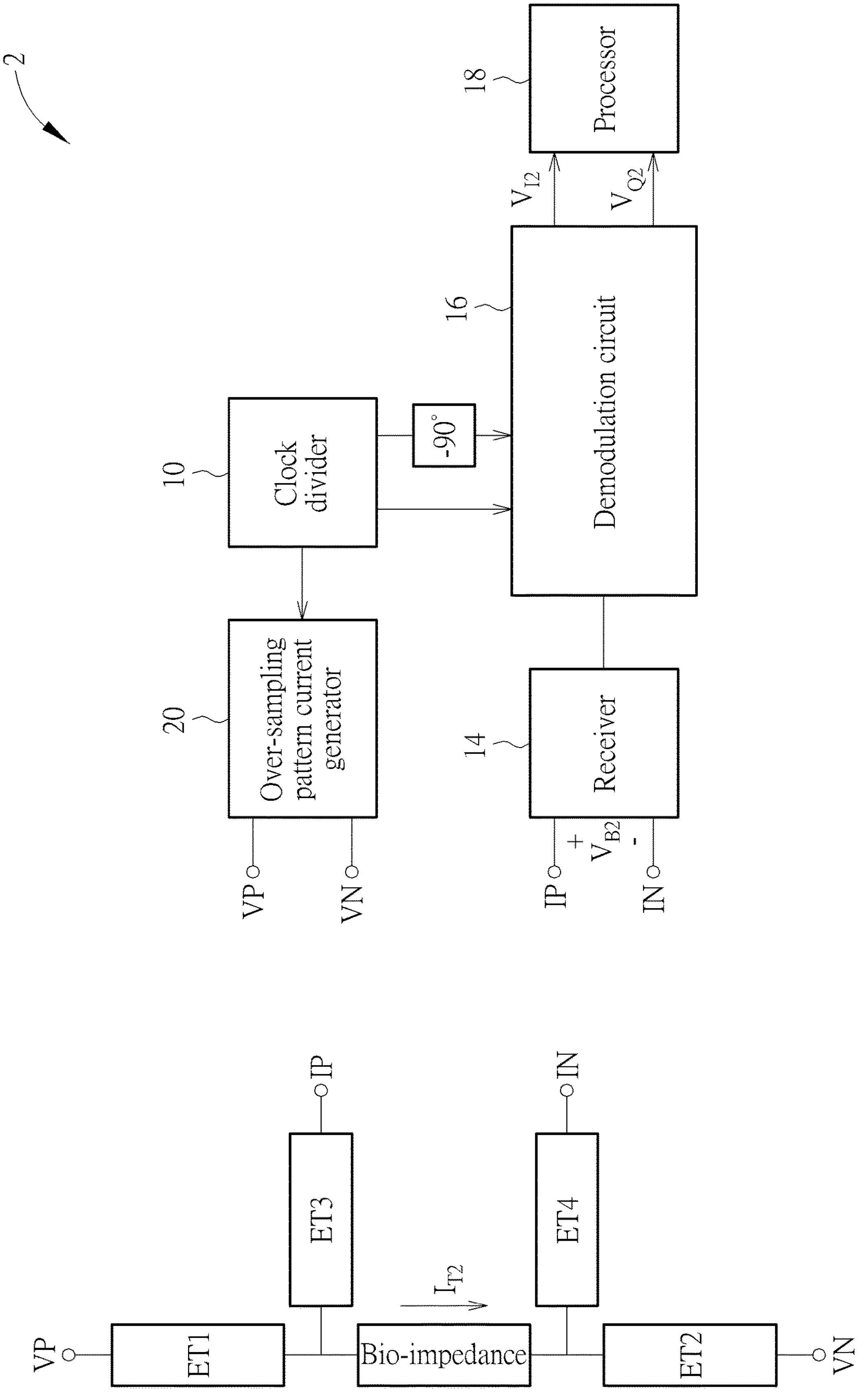
FIG. 3 is a schematic diagram of a bio-impedance measurement device according to an embodiment of the present invention.

In order to reduce the error in measuring the bio-impedance value including the resistive part, the capacitive part and the inductive part, the present invention provides a bio-impedance measurement system including a bio-impedance measurement device 2 and the bio-impedance, and utilizes a probing signal having an over-sampling pattern to measure the bio-impedance value of the bio-impedance. Please refer to FIG. 3. FIG. 3 is a schematic diagram of a bio-impedance measurement device 2 according to an embodiment of the present invention. The bio-impedance measurement device 2 is derived from the bio-impedance measurement device 1, so the same elements are represented by the same symbols. The difference between the bio-impedance measurement device 2 and the bio-impedance measurement device 1 is that the square wave current generator 12 is replaced by an over-sampling pattern current generator 20. Specifically, the over-sampling pattern current generator 20 is configured to generate a probing signal $I_{T2}$ according to the clock signals, and input the probing signal $I_{T2}$ having an over-sampling pattern and the specific frequency into the bio-impedance through electrodes ET1, ET2. The receiver 14 is configured to receive a response signal $V_{B2}$ related to the probing signal $I_{T2}$ from the bio-impedance through electrodes ET3, ET4. The demodulation circuit 16 is coupled to the clock divider 10 and the receiver 14, and configured to demodulate the response signal $V_{B2}$ to an in-phase signal $V_{I2}$ and a quadrature-phase signal $V_{Q2}$ according to the clock signals. The processor 18 is coupled to the demodulation circuit 16, and configured to analyze the probing signal $I_{T2}$, the in-phase signal $V_{I2}$ and the quadrature-phase signal $V_{Q2}$ to determine the bio-impedance value Z (nω).

Figure 4:
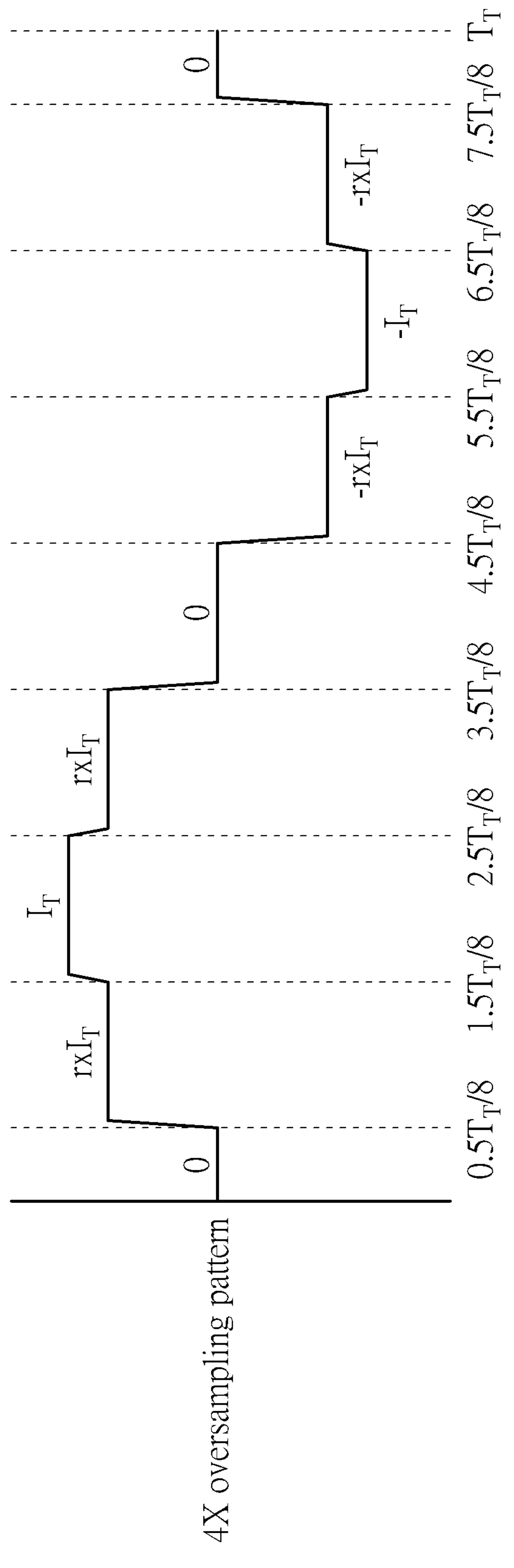
FIG. 4 is a waveform diagram of a probing signal having a 4× over-sampling pattern according to an embodiment of the present invention.
Figure 5:
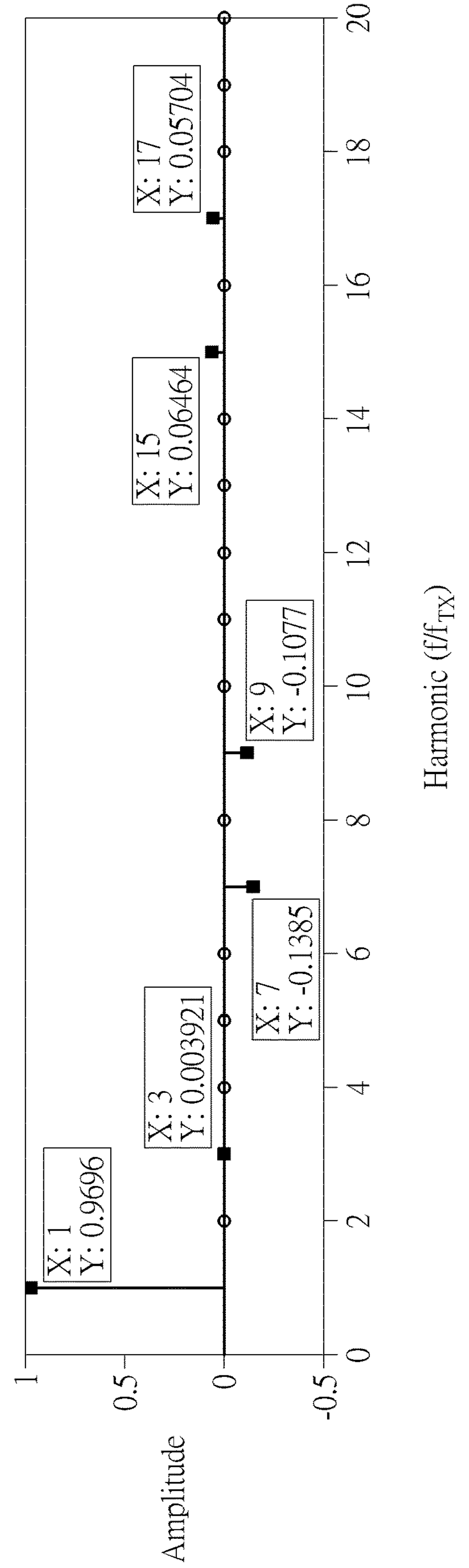
FIG. 5 is a spectrum diagram of an in-phase signal according to an embodiment of the present invention.

Specifically, by inputting the probing signal $I_{T2}$ having the over-sampling pattern, the high-order harmonics of the response signal $V_{B2}$ may be significantly reduced. In an embodiment, please refer to FIG. 4, which illustrates a waveform diagram of the probing signal $I_{T2}$ having a 4× over-sampling pattern according to an embodiment of the present invention. As shown in FIG. 4, the 4× over-sampling pattern is output in sequence 0, r*I, I, r*I, 0, −r*I, −I, −r*I. By appropriately selecting the r value, the high-order harmonics of the response signal $V_{B2}$ may be significantly reduced. For example, please refer to FIG. 5, which illustrates a spectrum diagram of the in-phase signal $V_{I2}$ with the probing signal having the 4× over-sampling pattern and the r value set to 0.7 according to an embodiment of the present invention. As shown in FIG. 5, a 3-rd harmonics of the in-phase signal $V_{I2}$ is 0.003921 and a 5-th harmonics of the in-phase signal $V_{I2}$ is −0.002353, which are respectively smaller than a 3-rd harmonics of the in-phase signal $V_{I1}$ as ⅓ and a 5-th harmonics of the in-phase signal $V_{I1}$ as ⅕ shown in equation (2). In this way, the error of the bio-impedance measurement device 2 in measuring the bio-impedance value may be significantly reduced as the high-order harmonics are reduced.

Figure 6:
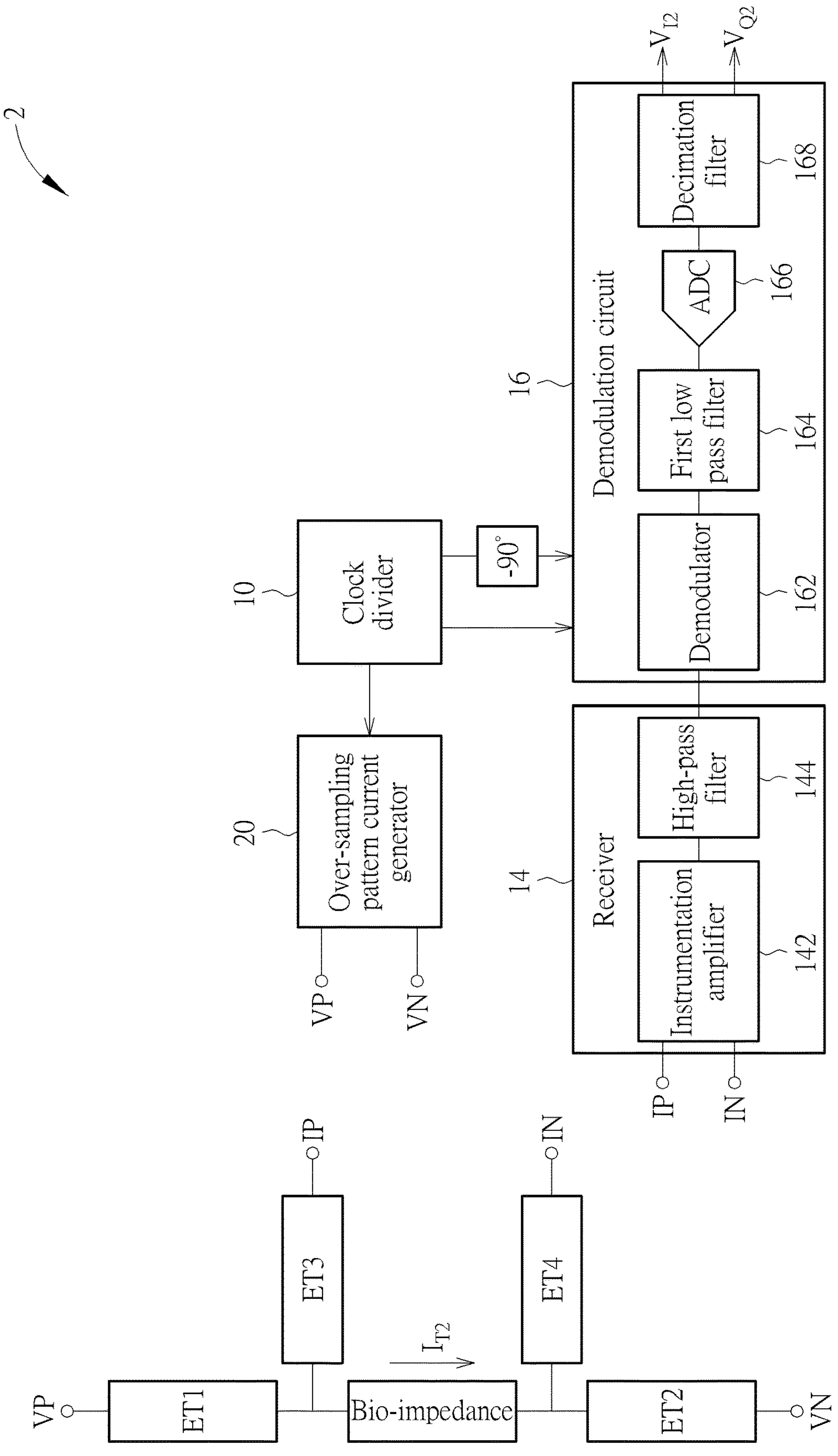
FIG. 6 is a schematic diagram of the receiver and the demodulation circuit of the bio-impedance measurement device according to an embodiment of the present invention.

It should be noted that the bio-impedance measurement device 2 is the embodiment of the present invention, those skilled in the art may make different modifications accordingly, and is not limited thereto. For example, FIG. 6 is a detailed schematic diagram of the receiver 14 and the demodulation circuit 16 of the bio-impedance measurement device 2 according to an embodiment of the present invention. The receiver 14 includes an instrumentation amplifier 142 with a high-pass filter 144. The demodulation circuit 16 includes a demodulator 162, a first low pass filter 164, an analog-to-digital convertor (ADC) 166 and a decimation filter 168. It should be noted that the operation principles of the instrumentation amplifier 142, the high-pass filter 144, the demodulator 162, the first low pass filter 164, the analog-to-digital convertor 166 and the decimation filter 168 are well known in the art, so it is not reiterated. For example, the instrumentation amplifier 142 is an improvement of a differential amplifier. The instrumentation amplifier 142 includes an input buffer and therefore does not require input impedance matching to be suitable for electronic measurement device to perform measurements.

Figure 7:
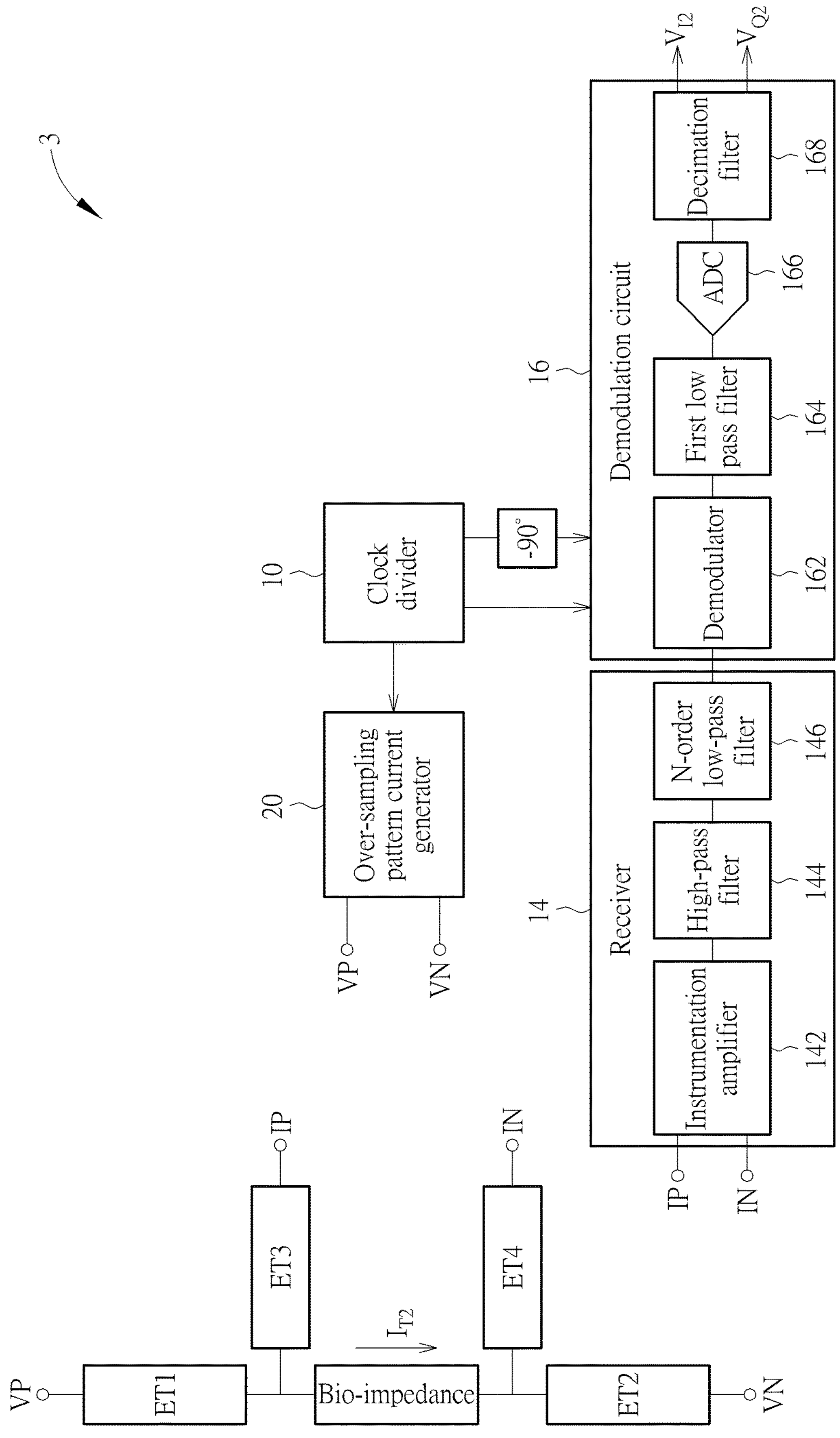
FIG. 7 is a schematic diagram of a bio-impedance measurement device according to an embodiment of the present invention.

Since the amplitudes of the 3-rd and the 5-th harmonics of the response signal have been greatly reduced by inputting the probing signal $I_{T2}$ having the over-sampling pattern, the present invention may also add an N-order low-pass filter behind the instrumentation amplifier 142 or between the receiver 14 and the demodulation circuit 16 to further reduce the amplitudes of all high-order harmonics of the response signal. Please refer to FIG. 7. FIG. 7 is a schematic diagram of a bio-impedance measurement device 3 according to an embodiment of the present invention. The bio-impedance measurement device 3 is derived from the bio-impedance measurement device 2, so the same elements are represented by the same symbols. The difference between the bio-impedance measurement device 3 and the bio-impedance measurement device 2 is that an N-order low-pass filter 146 is included between the high-pass filter 144 and the demodulation circuit 16. Specifically, the over-sampling pattern current generator 20 is configured to generate a probing signal $I_{T2}$ according to the clock signals, and input the probing signal $I_{T2}$ having the over-sampling pattern and the specific frequency into the bio-impedance through electrodes ET1, ET2. The receiver 14 is configured to receive a response signal $V_{B2}$ related to the probing signal $I_{T2}$ from the bio-impedance through electrodes ET3, ET4. The demodulation circuit 16 is coupled to the clock divider 10 and the receiver 14, and configured to demodulate the response signal $V_{B2}$ which is passed through the N-order low-pass filter 146 to an in-phase signal $V_{I3}$ and a quadrature-phase signal $V_{Q3}$ according to the clock signals. The processor 18 is coupled to the demodulation circuit 16, and configured to analyze the probing signal $I_{T2}$, the in-phase signal $V_{I3}$ and the quadrature-phase signal $V_{Q3}$ to determine the bio-impedance value Z (nω). It should be noted that a cutoff frequency of the N-order low-pass filter 146 may be set as twice of the specific frequency. In an embodiment, the in-phase signal $V_{I3}$ and the quadrature-phase signal $V_{Q3}$ may be expressed as the equation (5) and the equation (6)

$$V_{I3} = G\times I_{T1}|Z(\omega)|\cos(\theta_{\omega z}+\theta_{Ip})\times \frac{2}{\pi}\left[C_1 + C_3\frac{|Z(3\omega)|}{|Z(\omega)|}\frac{\cos(\theta_{3\omega z}+\theta_{3Ip})}{\cos(\theta_{\omega z}+\theta_{Ip})} + C_5\frac{|Z(5\omega)|}{|Z(\omega)|}\frac{\cos(\theta_{5\omega z}+\theta_{5Ip})}{\cos(\theta_{\omega z}+\theta_{Ip})} + \dots\right] \quad (5)$$

$$V_{Q3} = G\times I_{T1}|Z(\omega)|\sin(\theta_{\omega z}+\theta_{Ip})\times \frac{2}{\pi}\left[C_1 + C_3\frac{|Z(3\omega)|}{|Z(\omega)|}\frac{\sin(\theta_{3\omega z}+\theta_{3Ip})}{\sin(\theta_{\omega z}+\theta_{Ip})} + C_5\frac{|Z(5\omega)|}{|Z(\omega)|}\frac{\sin(\theta_{5\omega z}+\theta_{5Ip})}{\sin(\theta_{\omega z}+\theta_{Ip})} + \dots\right] \quad (6)$$

where $V_{I3}$ and $V_{Q3}$ represent the in-phase signal and the quadrature-phase signal, G represents a gain of the instrumentation amplifier 142, $I_{T1}$ represents the probing signal, a represents the angular frequency of the specific frequency, Z(nω) represents the bio-impedance value when the angular frequency is nω, $\theta_{n\omega}$ represents the phase of bio-impedance value when the angular frequency is nω, and $C_N$ represents an amplitude of the n-th harmonics.

In another embodiment, if the N-order low-pass filter 146 is set as a second-order low-pass filter, a transfer function of the second-order low-pass filter may be expressed as the equation (4):

$$TF_{LPF}(s) = \left(\frac{1}{1+\frac{s}{4\pi f_T}}\right)^2 \quad (4)$$

where $TF_{LPF}(S)$ represents the transfer function of the N-order low-pass filter 146, and $f_T$ represents the specific frequency.

Figure 8:
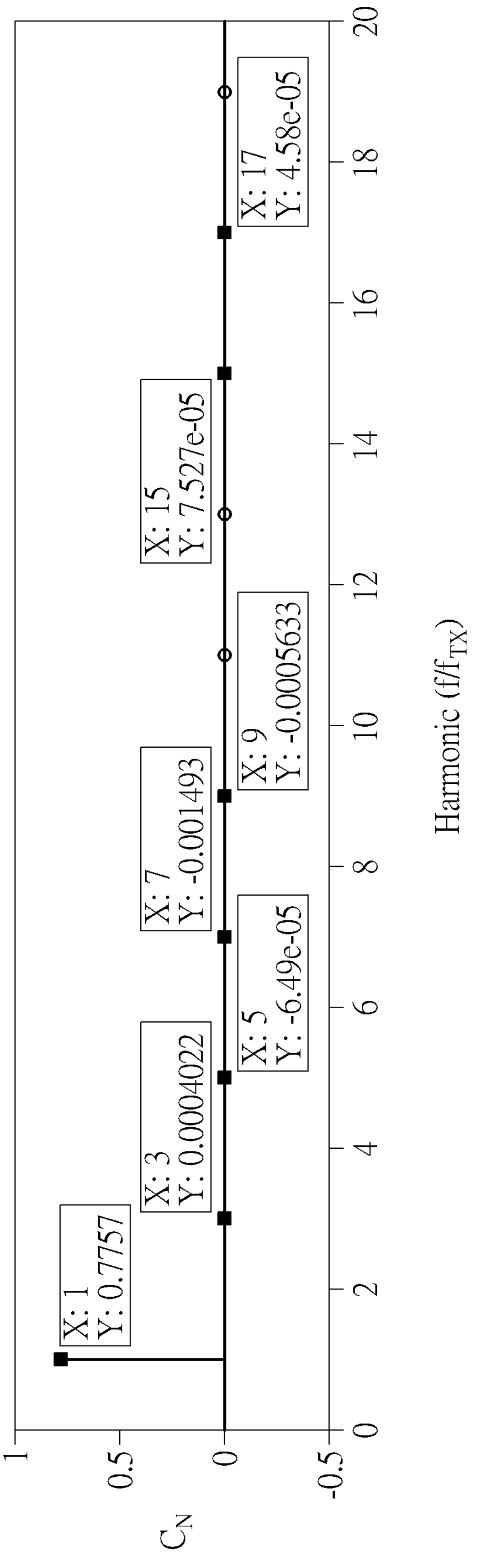
FIG. 8 is a spectrum diagram of an in-phase signal according to an embodiment of the present invention.

By passing through the second-order low-pass filter, the high-order harmonics of the response signal $V_{B2}$ may be significantly reduced. For example, please refer to FIG. 8, which illustrates a spectrum diagram of the in-phase signal $V_{I3}$ or the quadrature-phase signal $V_{Q3}$ with the probing signal having the 4X over-sampling pattern and the r value set to 0.7 according to an embodiment of the present invention. As shown in FIG. 8, a 3-rd harmonics coefficient c3 of the in-phase signal $V_{I3}$ is 0.0004022 and a 5-th harmonics coefficient c5 of the in-phase signal $V_{I3}$ is −0.0000649, which are respectively smaller than a 3-rd harmonics coefficient of the in-phase signal $V_I$ as ⅓ and a 5-th harmonics coefficient of the in-phase signal $V_I$ as ⅕ shown in equation (2). In this way, the error of the bio-impedance measurement device 3 in measuring the bio-impedance value may be significantly reduced as the high-order harmonics are reduced.

Figure 9:
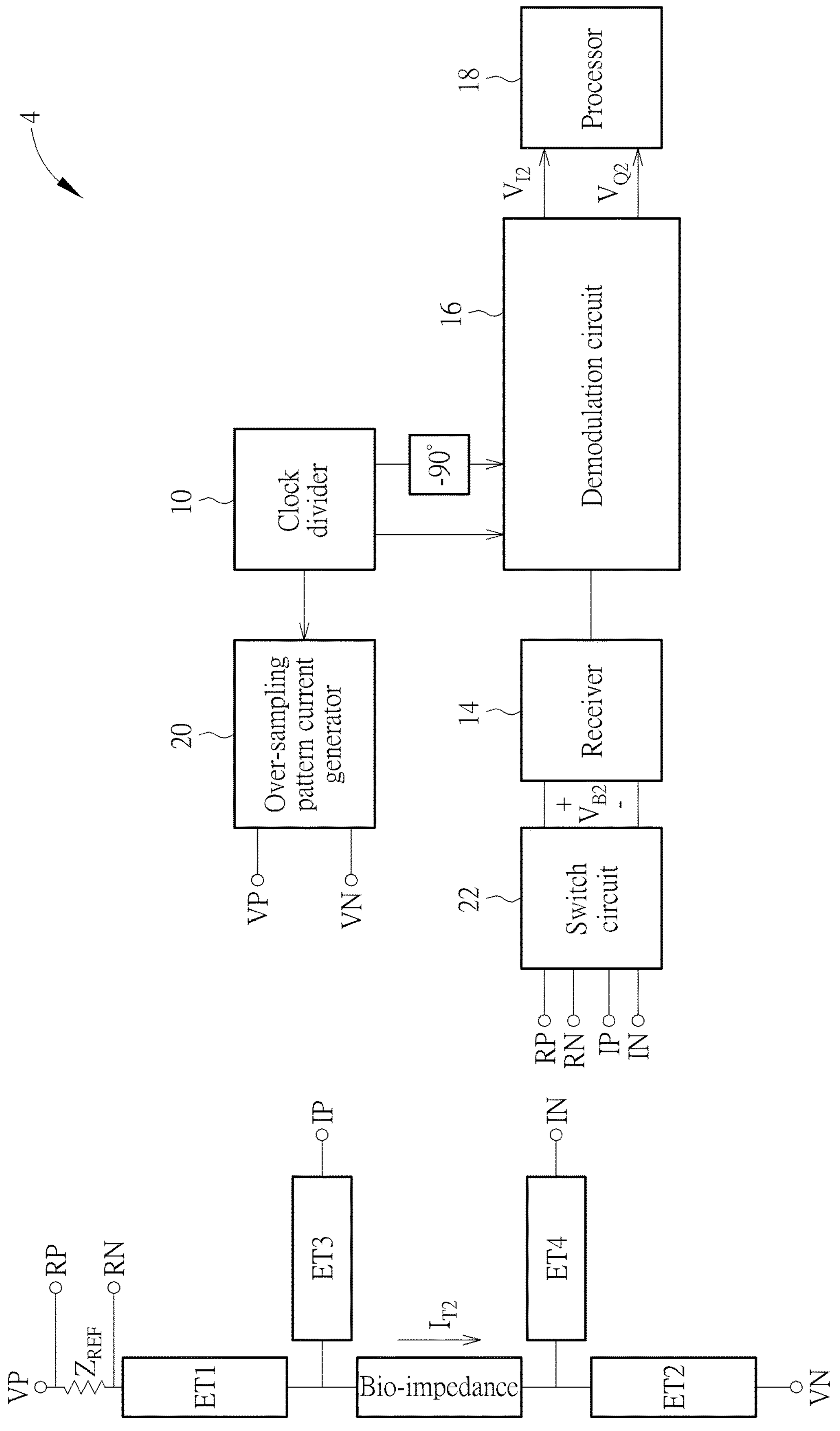
FIG. 9 is a schematic diagram of a bio-impedance measurement device according to an embodiment of the present invention.

On the other hand, in the bio-impedance measurement system, process errors may occur due to process variations in the gain of the instrumentation amplifier, the value of the probing signal, the specific frequency or the cutoff frequency, resulting in larger errors in measuring the bio-impedance. In order to reduce errors caused by the process variations, the bio-impedance measurement device of the present invention further measures a reference impedance independent of the process variations before measuring the bio-impedance to calibrate the bio-impedance value. Please refer to FIG. 9. FIG. 9 is a schematic diagram of a bio-impedance measurement device 4 according to an embodiment of the present invention. The bio-impedance measurement device 4 is derived from the bio-impedance measurement device 2, so the same elements are represented by the same symbols. The difference between the bio-impedance measurement device 4 and the bio-impedance measurement device 2 is that a reference impedance $Z_{REF}$ having a reference impedance value is connected in series between the over-sampling pattern current generator 20 and the bio impedance, and a switch circuit 22 is included between the receiver 14 and the bio-impedance or the reference impedance $Z_{REF}$. Specifically, the over-sampling pattern current generator 20 is configured to generate the probing signal $I_{T2}$ according to the clock signals, and input the probing signal $I_{T2}$ having the over-sampling pattern and the specific frequency into the reference impedance and the bio-impedance through electrodes ET1, ET2. The receiver 14 is configured to receive a reference response signal related to the probing signal $I_{T2}$ from the reference impedance or the response signal $V_{B2}$ related to the probing signal $I_{T2}$ from the bio-impedance through the switch circuit 22. The demodulation circuit 16 is coupled to the clock divider 10 and the receiver 14, and configured to demodulate the reference response signal to a reference in-phase signal and a reference quadrature-phase signal according to the clock signals, and demodulate the response signal $V_{B2}$ to the in-phase signal $V_{I2}$ and the quadrature-phase signal $V_{Q2}$ according to the clock signals. The processor 18 is coupled to the demodulation circuit 16, and configured to analyze the probing signal $I_{T2}$, the reference impedance value, the reference in-phase signal, the reference quadrature-phase signal, the in-phase signal $V_{I2}$ and the quadrature-phase signal $V_{Q2}$ to determine the bio-impedance value Z (nω). It should be noted that the bio-impedance measurement device 4 or the processor 18 may further include a memory to store the reference impedance value of the reference impedance and the measurement result of the reference impedance. Since the configurations of measuring the reference impedance $Z_{REF}$ and measuring the bio-impedance are exactly the same and the reference impedance $Z_{REF}$ is independent of the process variations, the measurement result of the reference impedance $Z_{REF}$ may be used to calibrate the measurement result of the bio-impedance. In this way, the error of the bio-impedance measurement device 4 in measuring the bio-impedance value may be reduced as the influence of the process variation is reduced. It should be noted that the calibration principle is well known in the art, so it is not reiterated.

Figure 10:
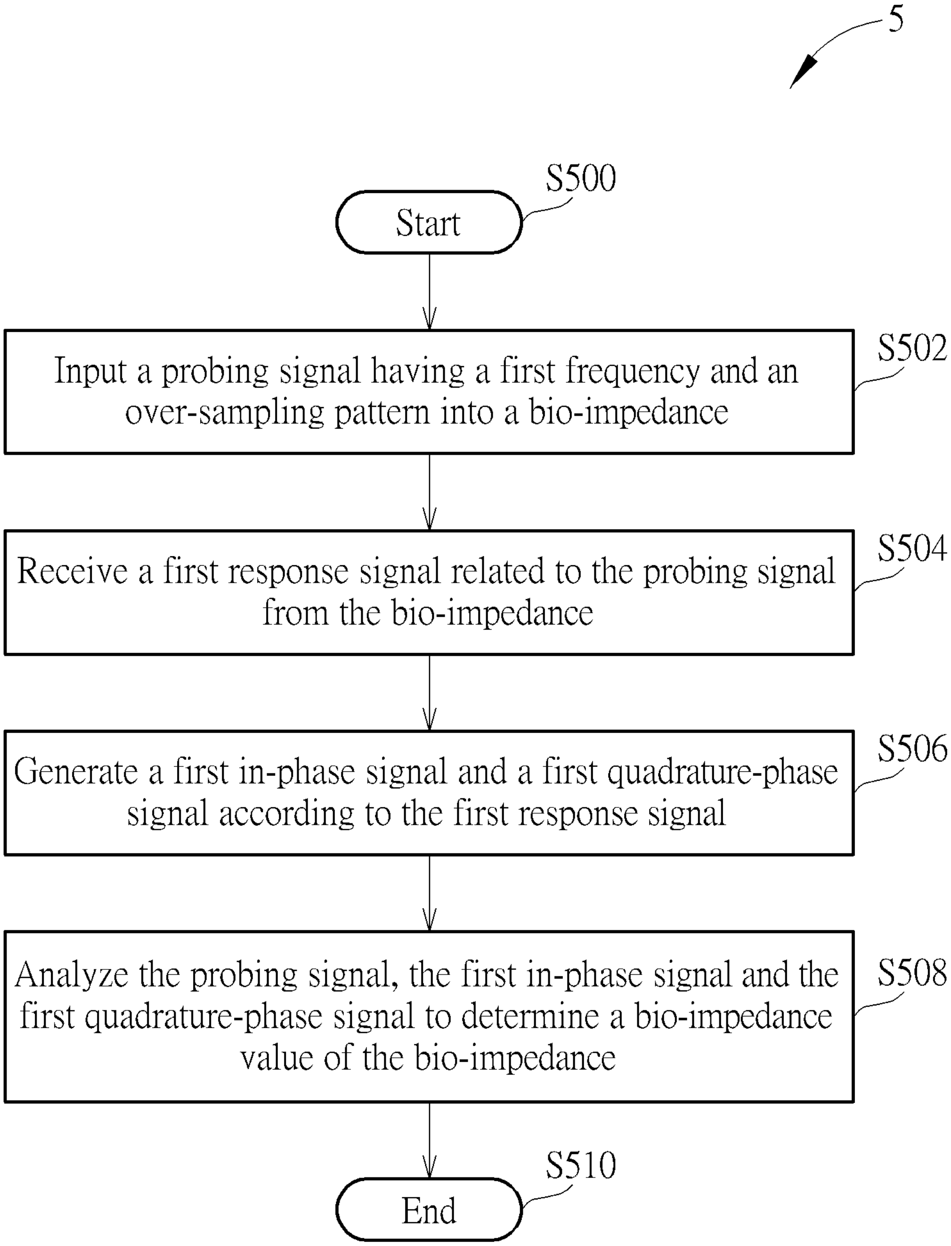
FIG. 10 is a flowchart of a bio-impedance measurement method according to an embodiment of the present invention.

The operations of the bio-impedance measurement devices 2-4 may be summarized as a bio-impedance measurement method 5, as shown in FIG. 10. The bio-impedance measurement method 5 includes the following steps:

Step S500: Start.

Step S502: Input a probing signal having a first frequency and an over-sampling pattern into a bio-impedance.

Step S504: Receive a first response signal related to the probing signal from the bio-impedance.

Step S506: Generate a first in-phase signal and a first quadrature-phase signal according to the first response signal.

Step S508: Analyze the probing signal, the first in-phase signal and the first quadrature-phase signal to determine a bio-impedance value of the bio-impedance.

Step S510: End.

The detail description and derivative changes of the bio-impedance measurement method 5 are described as above, and will not be reiterated.

It should be noted that the bio-impedance measurement devices 2-4 are different embodiments of the present invention. Those skilled in the art should readily make combinations, modifications and/or alterations on the abovementioned description and examples. The abovementioned description, steps, procedures and/or processes including suggested steps can be realized by means that could be hardware, software, firmware (known as a combination of a hardware device and computer instructions and data that reside as read-only software on the hardware device), an electronic system, or combination thereof. Examples of hardware can include analog, digital and mixed circuits known as microcircuit, microchip, or silicon chip. Examples of the electronic system may include a system on chip (SoC), system in package (SiP), a computer on module (CoM) and the computer system. Any of the abovementioned procedures and examples above may be compiled into program codes or instructions that are stored in the memory. The memory may include read-only memory (ROM), flash memory, random access memory (RAM), subscriber identity module (SIM), hard disk, or CD-ROM/DVD-ROM/BD-ROM, but not limited thereto. The processor 18 may read and execute the program codes or the instructions stored in the memory for realizing the abovementioned functions.

In summary, the bio-impedance measurement device and the bio-impedance measurement method of the present invention utilize a probing signal having an over-sampling pattern to measure the bio-impedance, and utilize an N-order low-pass filter to filter the high-order harmonics of the response signal, and further measure the reference impedance independent of the process variations to calibrate the measurement result of the bio-impedance. In this way, compared with the prior art, the measurement errors of the bio-impedance measurement device may be significantly reduced.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A bio-impedance measurement device, comprising:

a signal generator, configured to input a probing signal having a first frequency and an over-sampling pattern into a bio-impedance, wherein the probing signal comprises an oversampled current waveform including a plurality of sub-period current levels within one period of the first frequency, and wherein the oversampled current waveform is configured to reduce at least one odd-order harmonic component of a response signal associated with the probing signal;

a receiver, configured to receive a first response signal related to the probing signal from the bio-impedance;

a demodulation circuit, coupled to the receiver, configured to generate a first in-phase signal and a first quadrature-phase signal according to the first response signal; and a processor, coupled to the signal generator and the demodulation circuit, configured to analyze the probing signal, the first in-phase signal and the first quadrature-phase signal to determine a bio-impedance value of the bio-impedance.

2. The bio-impedance measurement device of claim 1, wherein the first response signal is a voltage signal.

3. The bio-impedance measurement device of claim 1, further comprising:

a low-pass filter, coupled between the receiver and the demodulation circuit, configured to filter the first response signal to generate a pre-processing signal;

wherein the demodulation circuit demodulates the pre-processing signal into the first in-phase signal and the first quadrature-phase signal.

4. The bio-impedance measurement device of claim 3, wherein a cutoff frequency of the low-pass filter is lower than a predetermined multiple of the first frequency.

5. The bio-impedance measurement device of claim 1, further comprising:

a reference impedance, coupled between the signal generator and the bio-impedance; and a memory, configured to store a reference impedance value of the reference impedance;

wherein the signal generator further inputs the probing signal having the first frequency and the over-sampling pattern into the reference impedance and the bio-impedance; the receiver further receives a second response signal related to the probing signal from the reference impedance; the demodulation circuit further generates a second in-phase signal and a second quadrature-phase signal according to the second response signal; and the processor further analyzes the probing signal, the reference impedance value, the first in-phase signal, the first quadrature-phase signal, the second in-phase signal and the second quadrature-phase signal to determine the bio-impedance value of the bio-impedance.

6. A bio-impedance measurement system, for measuring a bio-impedance, comprising:

a bio-impedance measurement device, configured to be coupled to the bio-impedance, wherein the bio-impedance measurement device is configured to input a probing signal having a first frequency and an over-sampling pattern into the bio-impedance, receive a first response signal related to the probing signal from the bio-impedance, generate a first in-phase signal and a first quadrature-phase signal according to the first response signal, and analyze the probing signal, the first in-phase signal and the first quadrature-phase signal to determine a bio-impedance value of the bio-impedance.

7. The bio-impedance measurement system of claim 6, wherein the first response signal is a voltage signal.

8. The bio-impedance measurement system of claim 6, wherein the bio-impedance measurement device is further configured to filter the first response signal to generate a pre-processing signal, and demodulate the pre-processing signal into the first in-phase signal and the first quadrature-phase signal.

9. The bio-impedance measurement system of claim 8, wherein a cutoff frequency for filtering the first response signal is lower than a predetermined multiple of the first frequency.

10. The bio-impedance measurement system of claim 6, wherein the bio-impedance measurement device is further configured to input the probing signal having the first frequency and the over-sampling pattern into a reference impedance and the bio-impedance; receive a second response signal related to the probing signal from the reference impedance; generate a second in-phase signal and a second quadrature-phase signal according to the second response signal; and analyze the probing signal, the reference impedance value, the first in-phase signal, the first quadrature-phase signal, the second in-phase signal and the second quadrature-phase signal to determine the bio-impedance value of the bio-impedance.

* * * * *